United States Patent [19]
Nickl et al.

[11] 3,969,523
[45] July 13, 1976

[54] ANTIPHLOGISTIC PHARMACEUTICAL COMPOSITIONS CONTAINING A 1-(NICOTINOYL OR ISONICOTINOYL)-3-BIPHENYLYL-ALKANONE-(2)

[75] Inventors: Josef Nickl; Helmut Teufel; Wolfhard Engel; Ernst Seeger; Günther Engelhardt, all of Biberach an der Riss, Germany

[73] Assignee: Boehringer Ingelheim GmbH, Ingelheim am Rhein, Germany

[22] Filed: Aug. 25, 1975

[21] Appl. No.: 607,667

Related U.S. Application Data

[62] Division of Ser. No. 474,181, May 29, 1974, Pat. No. 3,920,668.

[30] Foreign Application Priority Data

June 7, 1973 Germany............................ 2328973

[52] U.S. Cl. ................................................. 424/266
[51] Int. Cl.² ...................................... A61K 31/455
[58] Field of Search............................ 424/274, 266

Primary Examiner—Stanley J. Friedman
Attorney, Agent, or Firm—Hammond & Littell

[57] ABSTRACT

Pharmaceutical compositions containing a compound of the formula

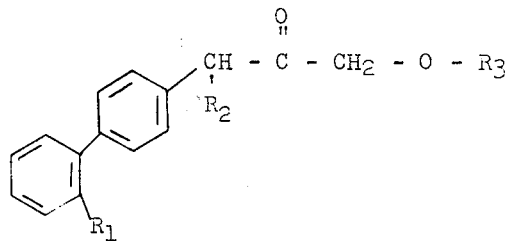

wherein
$R_1$ is hydrogen, fluoro or chloro,
$R_2$ is hydrogen or alkyl of 1 to 3 carbon atoms, and
$R_3$ is nicotinoyl or isonicotinoyl, or an optically active antipode thereof; and a method of using the same as antiphlogistics.

6 Claims, No Drawings

ANTIPHLOGISTIC PHARMACEUTICAL COMPOSITIONS CONTAINING A 1-(NICOTINOYL OR ISONICOTINOYL)-3-BIPHENYLYL-ALKANONE-(2)

This is a division of copending application Ser. No. 474,181, filed May 29, 1974, now U.S. Pat. No. 3,920,668 granted Nov. 18, 1975.

This invention relates to novel pharmaceutical compositions containing a 1-(nicotinoyl or isonicotinoyl)-3-biphenylyl-alkanone-(2), as well as to a method of using the same antiphlogistics.

More particularly, the present invention relates to antiphlogistic pharmaceutical compositions containing as an active ingredient a compound of the formula

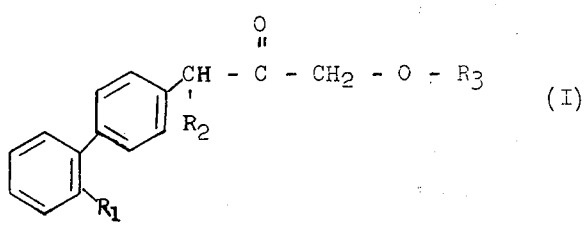

wherein
$R_1$ is hydrogen, fluoro or chloro,
$R_2$ is hydrogen or alkyl of 1 to 3 carbon atoms, and
$R_3$ is nicotinoyl or isonicotinoyl, or an optically active antipode thereof.

The compounds embraced by formula I may be prepared by the following method:

By decomposing a diazomethyl-ketone of the formula

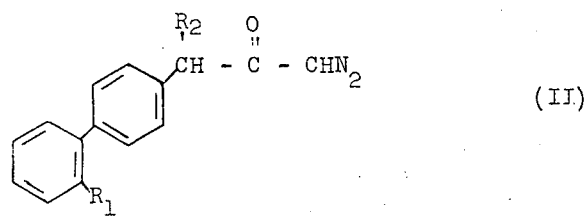

wherein $R_1$ and $R_2$ have the meanings defined above, in the presence of nicotinic or isonicotinic acid.

The reaction is advantageously performed in the presence of a water-miscible solvent such as tetrahydrofuran or dioxane, and at tempertures up to the boiling point of the solvent which is used, but preferably at temperatures from 50° to 100°C.

If the reaction is performed in the presence of a mineral acid such as sulfuric acid or phosphoric acid, a compound of formula I is obtained, wherein $R_3$ is hydrogen.

If the reaction is carried out in the presence of a carboxylic acid of the formula $R_3$ — OH         (III)

wherein $R_3$ has the meanings defined above, optionally in the presence of a catalyst, such as copper (II) choride, where the used organic acid of formula III or also an inert solvent, such as benzene, may serve as the solvent, a corresponding compound of formula I is obtained, wherein $R_3$ has the meanings defined above.

A compound of formula I, wherein $R_3$ is hydrogen, may be converted into the corresponding acyl derivative of the formula I by means of acylation, for example, with the corresponding acid halide, acid anhydride or with the corresponding acid in the presence of a chloroformic acid ester, preferably in the presence of an acid binding agent, such as triethylamine or pyridine.

The compounds of formula III used as starting materials are obtained by reaction of the corresponding biphenylyl-acetyl halides with diazomethane.

The following examples illustrate the preparation of compounds of the formula I and their optically active antipodes.

The thin-layer chromatograms were carried out on pre-prepared silica gel plates Polygram SIL G/UV of Macherey, Nagel & Co., if not otherwise stated.

EXAMPLE 1

1-Isonicotinoyloxy-3-(2'-fluoro-4''-biphenyl)-butanone-(2)

9.1 gm (0.04 mol) of isonicotinic acid anhydride were added to a solution of 8.2 gm (0.0318 mol) of 1-hydroxy-3-(2'-fluoro-4''-biphenylyl)-butanone-(2) in 50 ml of dry pyridine. The mixture was stirred for a further 2 hours at room temperature under exclusion of moisture; 150 ml of water were added; and the reaction product was extracted with ethyl acetate. The organic layer was washed thoroughly with water to remove the pyridine, dried and evaporated. The residue, a crystalline oil, was recrystallized from 30 ml of isopropanol, m.p. 95°–97°C, in a yield of 7.8 gm (68% of theory), of the formula

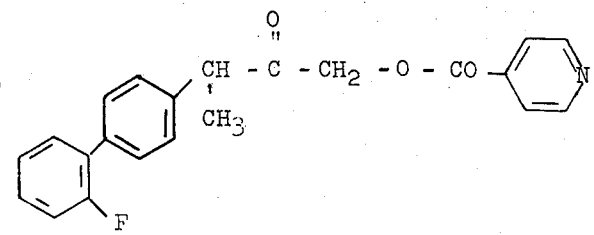

Elemental analysis: $C_{22}H_{18}FNO_3$ (363.35). Calculated: C — 72.17%; H — 4.99%; N — 3.86%. Found: C — 72.90%; H — 5.10%; N — 3.99%.

EXAMPLE 2

Using a procedure analogous to that described in Example 1, 1-isonicotinoyloxy-3-(4'-biphenylyl-butanone-(2), m.p. 89°–90°C (from ethanol), was prepared in a yield of 80% of theory, from 1-hydroxy-3-(4'-biphenylyl)-butanone-(2) and isonicotinic acid anhydride in pyridine.

EXAMPLE 3

Using a procedure analogous to that described in Example 1, 1-isonicotinoyloxy-3-(2'-chloro-4''-biphenylyl)-butanone-(2), was prepared in a yield of 78% of theory from 1-hydroxy-3-(2'-chloro-4''biphenylyl)-butanone-(2) and isonicotinic acid anhydride. The compound was purified by column chromatography on silica gel with benzene/ethyl acetate = 3/1, and was an oil with $R_f$-value: 0.3 (benzene/ethyl acetate = 3/1).

Elemental analysis: $C_{22}H_{18}ClNO$ (379.85). Calculated: C — 69.58%; H — 4.77%; N — 3.69%; Cl — 9.33%. Found: C — 70.30%; H — 5.17%; N — 3.48%; Cl — 8.44%.

EXAMPLE 4

Using a procedure analogous to that described in Example 1, 1-nicotinoyloxy-3-(2'-fluoro-4"-biphenyl)-butanone-(2), m.p. 89°–90°C (from isopropanol), was prepared in a yield of 81% of theory; from 1-hydroxy-3-(2'-fluoro-4"-biphenylyl)-butanone-(2) and nicotinoylchloride hydrochloride in pyridine, and had the formula

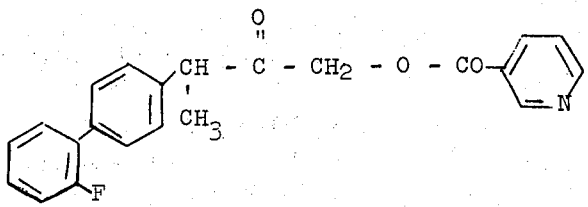

Elemental analysis: $C_{22}H_{18}FNO_3$ (363.35). Calculated: C — 72.71%; H — 4.99%; N — 3.86%. Found: C — 72.70%; H — 5.27%; N — 3.88%.

EXAMPLE 5

(+)-1-Isonicotinoyloxy-3-(2'-fluoro-4"-biphenylyl)-butanone-(2)

(a)

(+)-Diazomethyl-α-(2'-fluoro-4-biphenylyl)-ethyl-ketone 25.4 gm of (+)-2-(2'-fluoro-4"-biphenylyl)-propionic acid ($[\alpha]_D = +53°$ in methanol) were converted into the oily acid chloride by boiling with thionyl chloride. The acid chloride (31.1 gm = 0.118 mol), dissolved in 100 ml of benzene, was added dropwise to a solution of 0.26 mol of diazomethane in 490 ml of ether at a temperature below 10°C. After standing overnight, the mixture was evaporated in vacuo. The remaining oily diazomethyl-α-(2'-fluoro-4-biphenylyl)-ethyl-ketone had a $R_f$ value of 0.6 (Woelm preprepared silica gel plates F 254, eluens: ethylene chloride/ethyl acetate/glacial acetic acid = 100/30/5).

(b)

(+)-1-Hydroxy-3-(2'-fluoro-4"-biphenylyl)-butanone-(2)

15.8 gm of (+)-diazomethyl-α-(2'-fluoro-4-biphenylyl)-ethyl-ketone were dissolved in 240 ml of dioxane; 180 ml of 2N sulfuric acid were added, and the mixture was heated for 1 hour at 40°C. After all nitrogen had been formed, the solvent was removed in vacuo, the mixture was extracted with ethyl acetate, the organic layer was washed with water, dried and evaporated in vacuo. The oil obtained had an $R_f$ value of 0.48 (Woelm preprepared silica gel plates F 254, eluens: ethylene chloride/ethyl acetate/glacial acetic acid = 100/30/5). The yield was 88% of theory.

(c)

(+)-1-Isonicotinoyloxy-3-(2'-fluoro-4"-biphenylyl)-butanone-(2)

was prepared using a procedure analogous to that described in Example 1 from (+)-1-hydroxy-3-(2'-fluoro-4"-biphenylyl)-butanone-(2) and isonicotinic acid anhydride. The yield was 47% of theory and the compound had a m.p. of 102°C and $[\alpha]_D^{23} = +215°$ in methanol (C = 0.55).

Elemental analysis: $C_{22}H_{18}FNO_3$ (363.35). Calculated: C — 72.71%; H — 4.99%; N — 3.86%. Found: C — 72.50%; H — 5.13%; N — 3.86%.

EXAMPLE 6

Using a procedure analogous to that described in Example 5(b), (−)-1-hydroxy-3-(2'-fluoro-4"-biphenylyl)-butanone-(2) was prepared in a yield of 85% of theory from (−)-diazomethyl-α-(2'-fluoro-4-biphenyly)-ethyl-ketone [oil, $R_f$-value: 0.6 (Woelm preprepared silica gel plates F 254; eluens: ethylene chloride/ethyl acetate/glacial acetic acid = 100/30/5)]. This compound was an oil, $R_f$-value: 0.50 (Woelm preprepared silica gel plates F 254; eluens: ethylene chloride/ethyl acetate/glacial acetic acid = 100/30/5).

EXAMPLE 7

Using a procedure analogous to that described in Example 1, (−)-1-isonicotinoyloxy-3-(2'-fluoro-4"-biphenylyl)-butanone-(2), m.p. 99°–101°C, was prepared in a yield of 30% of theory from (−)-1-hydroxy-3-(2'-fluoro-4"-biphenylyl-butanone-(2) and isonicotinic acid anhydride. $[\alpha]_D^{23} = −217°$ in methanol (c= 0.47).

Elemental analysis: $C_{22}H_{18}FNO_3$ (363.35). Calculated: C — 72.71%; H — 4.99%; N — 3.86%. Found: C — 72.70%; H — 4.97%; N — 3.91%.

The compounds embraced by formula I above and their optically active antipodes have useful pharmacodynamic properties. More particularly, they exhibit antiphlogistic activity with surprisingly small ulcerogenic side-effects in warm-blooded animals, such as rats.

The pharmacodynamic activity of the compounds of the formula I, namely their antiphlogistic activity with a surprisingly small ulcerogenic side-effect, was ascertained in the manner described below, and some illustrative test results are shown in the table, where A = 1-isonicotinoyloxy-3-(2'-fluoro-4"-biphenylyl)-butanone-(2).

Antiphlogistic activity:

The antiphlogistic activity was tested to determine the antiexsudative effect on the kaolin-induced edema (see Hillebrecht in Arzneimittelforschung 4, 607 – 614 (1954) and the carrageenin-induced edema (see Winter in Proc. Soc. Exper. Biol. Med. 111, 544 (1962)) of the hind paw of the rat after oral administration of at least 3 doses to at least 10 animals per dose. The dose leading to a 35% reduction of the swelling ($ED_{35}$) was graphically determined.

Ulcerogenic activity:

The ulcerogenic activity in the rat was determined after oral administration of the compound for 3 times after 24 hours each time. The animals were killed 4 hours after that, and the number of the animals having an ulcer was recorded. The dose which caused an ulcer in 50% of the animals ($ED_{50}$) was graphically determined.

Acute toxicity:

The peroral acute toxicity of the compounds was determined on groups of 10 rats each. The $LD_{50}$, i.e. the dose administered perorally after which 50% of the animals died within a period of 14 days, was calculated according to the method of Litchfield and Wilcoxon. The results are shown below in Table I.

TABLE I

| Compound | ED$_{35}$ mgm/kg p.o. kaolin induced edema | ED$_{35}$ mgm/kg p.o. carragenin induced edema | ED$_{50}$ mgm/kg p.o. ulcer activity | LD$_{50}$ mgm/kg p.o. |
|---|---|---|---|---|
| A | 14 | 22.5 | 71 | 1,170 |

For pharmaceutical purposes the compounds of the formula I are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective single dosage unit of the compounds of the formula I is from 1.67 to 6.67 mgm/kg body weight, preferably 2.5 to 5.0 mgm/kg body weight.

The following examples illustrate a few pharmaceutical dosage unit compositions comprising a compound of the formula I as an active ingredient and represent the best modes contemplated of putting the invention into practical use. The parts are parts by weight unless otherwise specified.

EXAMPLE 8

Tablets

The tablet composition was compounded from the following ingredients:

| 1-Isonicotinoyloxy-3-(2'-fluoro-4''-biphenylyl)-butanone-(2) | 200.0 parts |
| Corn starch | 97.0 parts |
| Polyvinyl pyrrolidone | 10.0 parts |
| Magnesium stearate | 3.0 parts |
| Total | 310.0 parts |

Preparation:

The mixture of active ingredient with corn starch was granulated by passing through a 1.5 mm screen with an aqueous 14% solution of polyvinylpyrrolidone, dried at 45°C and again passed through the said screen. The granulate thus prepared was mixed with magnesium stearate and compressed into 310 mgm tablets. Each tablet contained 200 mgm of the butanone compound, and was an oral dosage unit composition with effective antiphlogistic activity.

EXAMPLE 9

Coated tablets

The tablet core composition was compounded from the following ingredients:

| 1-Nicotinoyloxy-3-(2'-fluoro-4''-biphenylyl)-butanone-(2) | 200.0 parts |
| Corn starch | 70.0 parts |
| Gelatin | 8.0 parts |
| Talcum | 18.0 parts |
| Magnesium stearate | 4.0 parts |
| Total | 300.0 parts |

Preparation:

A mixture of the active ingredient with corn starch was granulated by passing it through a 1.5 mm screen with an aqueous 10% solution of the gelatin, dried at 45°C, and again passed through said screen. The granulate obtained was mixed with talcum and magnesium stearate and compressed to form the tablet cores, each having a weight of 300 mgm. The tablet cores were coated in known manner with a coating primarily of sugar and talcum and then polished with beeswax. Each coated tablet weighed 580 mgm and contained 200 mgm of the butanone compound, and was an oral dosage unit composition with effective antiphlogistic activity.

EXAMPLE 10

Gelatin capsules

The capsule contents were compounded from the following ingredients:

| 1-Nicotinoyloxy-3-(2'-fluoro-4''-biphenylyl)-propanone-(2) | 200.0 parts |
| Corn starch | 190.0 parts |
| Aerosil | 6.0 parts |
| Magnesium stearate | 4.0 parts |
| Total | 400.0 parts |

Preparation:

The ingredients were homogeneously mixed and 400 mgm portions were filled into size No. 1 gelatin capsules. Each gelatin capsule contained 200 mgm of the propanone compound and was an oral dosage unit composition with effective antiphlogistic activity.

EXAMPLE 11

Suppositories

The suppository composition was compounded from the following ingredients:

| 1-Isonicotinoyloxy-3-(2'-fluoro-4''-biphenylyl)-butanone-(2) | 100.0 parts |
| Suppository base (e.g. cocoa butter) | 1450.0 parts |
| Total | 1550.0 parts |

Preparations:

The active ingredient was finely powdered and stirred into the molten suppository base at 40°C, using an immersion homogenizer. 1550 mgm portions of the mixture at 38°C were poured into cooled suppository molds and allowed to cool therein. Each suppository contained 100 mgm of the butanone compound and was a rectal dosage unit composition with effective antiphlogistic activity.

Analogous results are obtained when any one of the other compounds embraced by formula I or an optically active antipode thereof is substituted for the particular ketone in Example 8 through 11. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. An antiphlogistic pharmaceutical dosage unit composition consisting essentially of an inert pharmaceutical carrier and an effective antiphlogistic amount of a compound of the formula

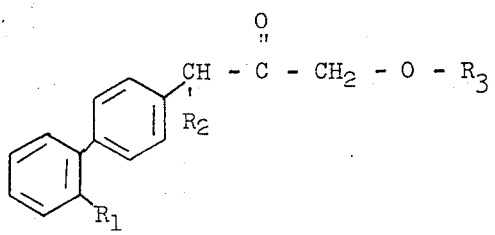

wherein
R$_1$ is hydrogen fluoro or chloro,
R$_2$ is hydrogen or alkyl of 1 to 3 carbon atoms, and
R$_3$ is nicotinoyl or isonicotinoyl, or an optically active antipode thereof.
2. A composition of claim 1, wherein said compound is 1-nicotinoyloxy-3-(2'-fluoro-4''-biphenylyl)-butanone-(2) or an optically active antipode thereof.
3. A composition of claim 1, wherein said compound is 1-nicotinoyloxy-3-(2'-fluoro-4''-biphenylyl)-butanone-(2) or an optically active antipode thereof.

4. The method of combatting inflammation in a warm-blooded animal, which comprises administering to said animal an effective antiphlogistic amount of a compound of the formula

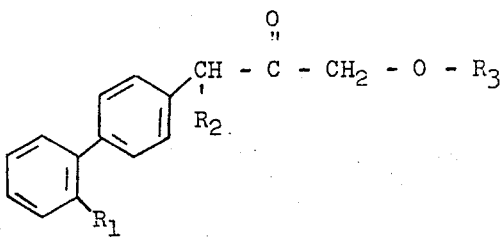

wherein
R$_1$ is hydrogen, fluoro or chloro,
R$_2$ is hydrogen or alkyl of 1 to 3 carbon atoms, and
R$_3$ is nicotinoyl or isonicotinoyl, or an optically active antipode thereof.
5. The method of claim 4, wherein said compound is 1-isonicotinoyloxy-3-(2'-fluoro-4''-biphenylyl)-butanone-(2) or an optically active antipode thereof.
6. The method of claim 4, wherein said compound is 1-nicotinoyloxy-3-(2'-fluoro-4''-biphenylyl)-butanone-(2) or an optically active antipode thereof.

* * * * *

UNITED STATES PATENT OFFICE
CERTIFICATE OF CORRECTION

Patent No. 3,969,523  Dated July 13, 1976

Inventor(s) JOSEF NICKL, HELMUT TEUFEL, WOLFHARD ENGEL, ERNST SEEGER, GUNTHER ENGELHARDT It is certified that error appears in the above-identified patent and that said Letters Patent are hereby corrected as shown below:

| | |
|---|---|
| Col. 1, line 15 | "same antiphlogistics" should read -- same as antiphlogistics -- |
| Col. 1, lines 65-66 | "choride" should read -- chloride -- |
| Col. 7, line 23 | "1-nicotinoyloxy-" should read -- 1-isonicotinoyloxy- -- |

Signed and Sealed this

Twenty-first Day of September 1976

[SEAL]

Attest:

RUTH C. MASON
Attesting Officer

C. MARSHALL DANN
Commissioner of Patents and Trademarks